United States Patent
Fulkerson

[11] Patent Number: 5,873,848
[45] Date of Patent: Feb. 23, 1999

[54] ORTHOPEDIC BRACE

[75] Inventor: John P. Fulkerson, Litchfield, Conn.

[73] Assignee: DePuy, Inc., Warsaw, Ind.

[21] Appl. No.: 663,913

[22] Filed: Jun. 14, 1996

[51] Int. Cl.$^6$ .................................................. A61F 5/00
[52] U.S. Cl. .............................. 602/62; 602/26; 602/63
[58] Field of Search .................................. 602/5, 23, 26, 602/60, 62, 63

[56] References Cited

U.S. PATENT DOCUMENTS

| | | |
|---|---|---|
| D. 307,054 | 4/1990 | Johnson, Jr. . |
| 3,046,981 | 7/1962 | Biggs, Jr. et al. . |
| 3,575,166 | 4/1971 | Rosman et al. . |
| 3,581,741 | 6/1971 | Rosman et al. . |
| 3,831,467 | 8/1974 | Moore . |
| 3,853,123 | 12/1974 | Moore . |
| 4,176,665 | 12/1979 | Terpening . |
| 4,201,203 | 5/1980 | Applegate . |
| 4,241,730 | 12/1980 | Helfet . |
| 4,250,578 | 2/1981 | Barlow . |
| 4,275,716 | 6/1981 | Scott, Jr. . |
| 4,287,884 | 9/1981 | Applegate . |
| 4,287,885 | 9/1981 | Applegate . |
| 4,296,744 | 10/1981 | Palumbo . |
| 4,334,528 | 6/1982 | Gauvry . |
| 4,353,362 | 10/1982 | DeMarco . |
| 4,366,813 | 1/1983 | Nelson . |
| 4,370,977 | 2/1983 | Mauldin et al. . |
| 4,370,978 | 2/1983 | Palumbo . |
| 4,372,298 | 2/1983 | Lerman . |
| 4,407,276 | 10/1983 | Bledsoe . |
| 4,423,720 | 1/1984 | Meier et al. . |
| 4,433,679 | 2/1984 | Mauldin et al. . |
| 4,445,505 | 5/1984 | Labour et al. . |
| 4,466,428 | 8/1984 | McCoy . |
| 4,487,200 | 12/1984 | Feanny et al. . |
| 4,494,534 | 1/1985 | Hutson . |
| 4,503,846 | 3/1985 | Martin . |
| 4,572,170 | 2/1986 | Cronk et al. . |
| 4,607,628 | 8/1986 | Dashefsky . |
| 4,624,247 | 11/1986 | Ford . |
| 4,632,097 | 12/1986 | Brooks . |
| 4,633,867 | 1/1987 | Kausek et al. . |
| 4,635,623 | 1/1987 | Charuest et al. . |
| 4,693,241 | 9/1987 | Trznadel . |
| 4,723,322 | 2/1988 | Shelby . |
| 4,733,656 | 3/1988 | Marquette . |
| 4,765,318 | 8/1988 | Tranberg et al. . |
| 4,777,946 | 10/1988 | Watanabe et al. . |
| 4,781,179 | 11/1988 | Colbert . |

(List continued on next page.)

FOREIGN PATENT DOCUMENTS

PCT WO
94/00082 1/1994 WIPO .

*Primary Examiner*—Richard J. Apley
*Assistant Examiner*—Kim M. Lee
*Attorney, Agent, or Firm*—Barnes & Thornburg

[57] ABSTRACT

An orthopedic brace includes a first strap, a second strap, and a support member. The first strap is covered on one side with loop material from a hook and loop-type fastener. A section of hook material is secured to the opposite side of the first strap. Similarly, the second strap has loop material secured to one side thereof, and a hook portion secured to the opposite side. The second strap is shorter than the first strap. The support member includes a body segment with a support pad removably secured thereto. A pair of support straps extend from the body. One side of each support strap includes both loop material and a segment of hook material secured thereto. The side of the body opposite the hook and loop material of the support straps is likewise covered with loop material and includes two hook material portions. In use, the first strap is wrapped around one portion of the limb above a joint and the second strap is wrapped around another portion of the limb below the joint. The support member is then wrapped around the limb such that the support pad is disposed adjacent the joint and one support strap is secured to the first strap above the joint and the other support strap is secured to the second strap below the joint.

34 Claims, 4 Drawing Sheets

U.S. PATENT DOCUMENTS

| | | |
|---|---|---|
| 4,790,299 | 12/1988 | Marquette . |
| 4,793,333 | 12/1988 | Marquette . |
| 4,854,308 | 8/1989 | Drillio . |
| 4,856,501 | 8/1989 | Castillo et al. . |
| 4,870,956 | 10/1989 | Fatool et al. . |
| 4,886,054 | 12/1989 | Castillo et al. . |
| 4,940,044 | 7/1990 | Castillo . |
| 4,961,416 | 10/1990 | Moore et al. . |
| 4,986,264 | 1/1991 | Miller . |
| 5,009,223 | 4/1991 | DeFonce . |
| 5,016,521 | 5/1991 | Bender . |
| 5,018,514 | 5/1991 | Grood et al. . |
| 5,036,837 | 8/1991 | Mitchell et al. . |
| 5,038,763 | 8/1991 | Wiggins . |
| 5,042,464 | 8/1991 | Skwor et al . |
| 5,052,375 | 10/1991 | Stark et al. . |
| 5,056,535 | 10/1991 | Bonnell . |
| 5,107,824 | 4/1992 | Rogers et al. . |
| 5,121,747 | 6/1992 | Andrews . |
| 5,133,341 | 7/1992 | Singer et al. . |
| 5,135,469 | 8/1992 | Castillo . |
| 5,139,476 | 8/1992 | Peters . |
| 5,139,477 | 8/1992 | Peters . |
| 5,168,577 | 12/1992 | Detty . |
| 5,221,252 | 6/1993 | Caprio, Jr. et al. . |
| 5,230,697 | 7/1993 | Castillo et al. . |
| 5,261,871 | 11/1993 | Greenfield . |
| 5,267,946 | 12/1993 | Singer et al. . |
| 5,277,697 | 1/1994 | France et al. . |
| 5,288,287 | 2/1994 | Castillo et al. . |
| 5,302,169 | 4/1994 | Taylor . |
| 5,334,135 | 8/1994 | Grim et al. . |
| 5,344,390 | 9/1994 | Motloch . |
| 5,358,469 | 10/1994 | Patchel et al. . |
| 5,368,546 | 11/1994 | Stark et al. . |
| 5,378,224 | 1/1995 | Billotti . |
| 5,383,845 | 1/1995 | Nebolon . |
| 5,399,152 | 3/1995 | Habermeyer et al. . |
| 5,399,153 | 3/1995 | Caprio, Jr. et al. . |
| 5,400,806 | 3/1995 | Taylor . |
| 5,403,350 | 4/1995 | McAtee . |
| 5,417,646 | 5/1995 | Gauvry . |
| 5,431,623 | 7/1995 | Rice . |
| 5,433,699 | 7/1995 | Smith, III . |
| 5,449,341 | 9/1995 | Harris . |
| 5,451,201 | 9/1995 | Prengler . |
| 5,456,722 | 10/1995 | McLeod et al. . |
| 5,462,517 | 10/1995 | Mann . |
| 5,472,413 | 12/1995 | Detty . |
| 5,474,524 | 12/1995 | Carey . |
| 5,484,389 | 1/1996 | Stark et al. . |
| 5,512,039 | 4/1996 | White . |
| 5,613,943 | 3/1997 | Palumbo .................................... 602/62 |

5,873,848

ORTHOPEDIC BRACE

BACKGROUND AND SUMMARY OF THE INVENTION

The present invention relates to orthopedic braces and, in particular, an orthopedic brace with improved force distribution.

Numerous orthopedic braces are known in the prior art. Examples of such braces used to support a human patella are shown in U.S. Pat. Nos. 4,296,744; 4,423,720 and 5,277,697. Each of these patents discloses a patella brace in which straps are used to secure the brace about a person's leg. In each device, the straps, after wrapping around the person's leg, are secured, directly or indirectly, to the same portion of the brace from which they originate. Thus, although the braces are intended to apply pressure to one side of the patella, the manner in which the straps are secured to the device actually creates a force on the brace in the opposite direction. This reduces the effectiveness of such a brace.

Accordingly, it is an object of the present invention to provide an orthopedic brace to provide support to a portion of the human anatomy.

Another object of the present invention is to provide a brace that will lessen forces applied to a portion of the human anatomy that run counter to the force intended to be applied.

Yet another object of the present invention is the provision of a flexible brace.

Still another object of the present invention is the provision of a brace that is easy to secure to a human limb.

These and other objects of the present invention are attained by the provision of a brace having a first strap and a first fastener for securing the first strap to a limb and a second strap and a second fastener for securing the second strap to a limb. The brace further includes a support member including a body portion and a support pad secured to the body portion. First and second support straps extend from the body portion. Third and fourth fasteners are provided for securing the first and second support straps to the first and second straps, respectively.

According to another embodiment of the present invention, a knee brace includes a first strap encircling a portion of the leg above the knee, a second strap encircling a portion of the leg below the knee and a support member providing a support pad for engaging the patella. A first support strap extends from the support member and encircles a portion of the leg above the knee. A second support strap extends from the support member and encircles a portion of the leg below the knee. The first support strap is attached to the first strap and the second support strap is attached to the second strap. The support member is reversible to allow the support pad to engage the patella from either the lateral or medial side.

According to another aspect of the invention, hook and loop-type fastener is used for attaching the first support strap to the first strap and the second support strap to the second strap.

According to another aspect of the invention, the first and second straps are independent of the support member. The support straps may be elastic.

According to another aspect of the invention, the first support strap extends spirally up the leg to attach to the first strap and the second support strap extends spirally down the leg to attach to the second strap.

According to another aspect of the invention, the first support strap encircles a portion of the leg, attaches to the support member and extends spirally up the leg to attach to the first strap and the second support strap encircles a portion of the leg, attaches to the support member and extends spirally down the leg to attach to the second strap.

According to another aspect of the invention, a knee brace includes a first anchor for attachment to the leg above the knee, a second anchor for attachment to the leg below the knee, a support member providing a support pad for engaging the patella, a first support strap for attaching the support member to the first anchor, and a second support strap for attaching the support member to the second anchor.

According to another aspect of the present invention, the first and second anchors are independent of the support member.

According to another aspect of the invention, the first support strap extends spirally up the leg to attach to the first anchor and the second support strap extends spirally down the leg to attach to the second anchor.

According to another aspect of the invention, the first support strap encircles a portion of the leg, attaches to the support member and extends spirally up the leg to attach to the first anchor and the second support strap encircles a portion of the leg, attaches to the support member and extends spirally down the leg to attach to the second anchor.

Other objects, advantages and features of the present invention will be apparent from the following Detailed Description of the Preferred Embodiments and accompanying drawings.

DETAILED DESCRIPTION OF THE PREFERRED EMBODIMENTS

Figure 1:
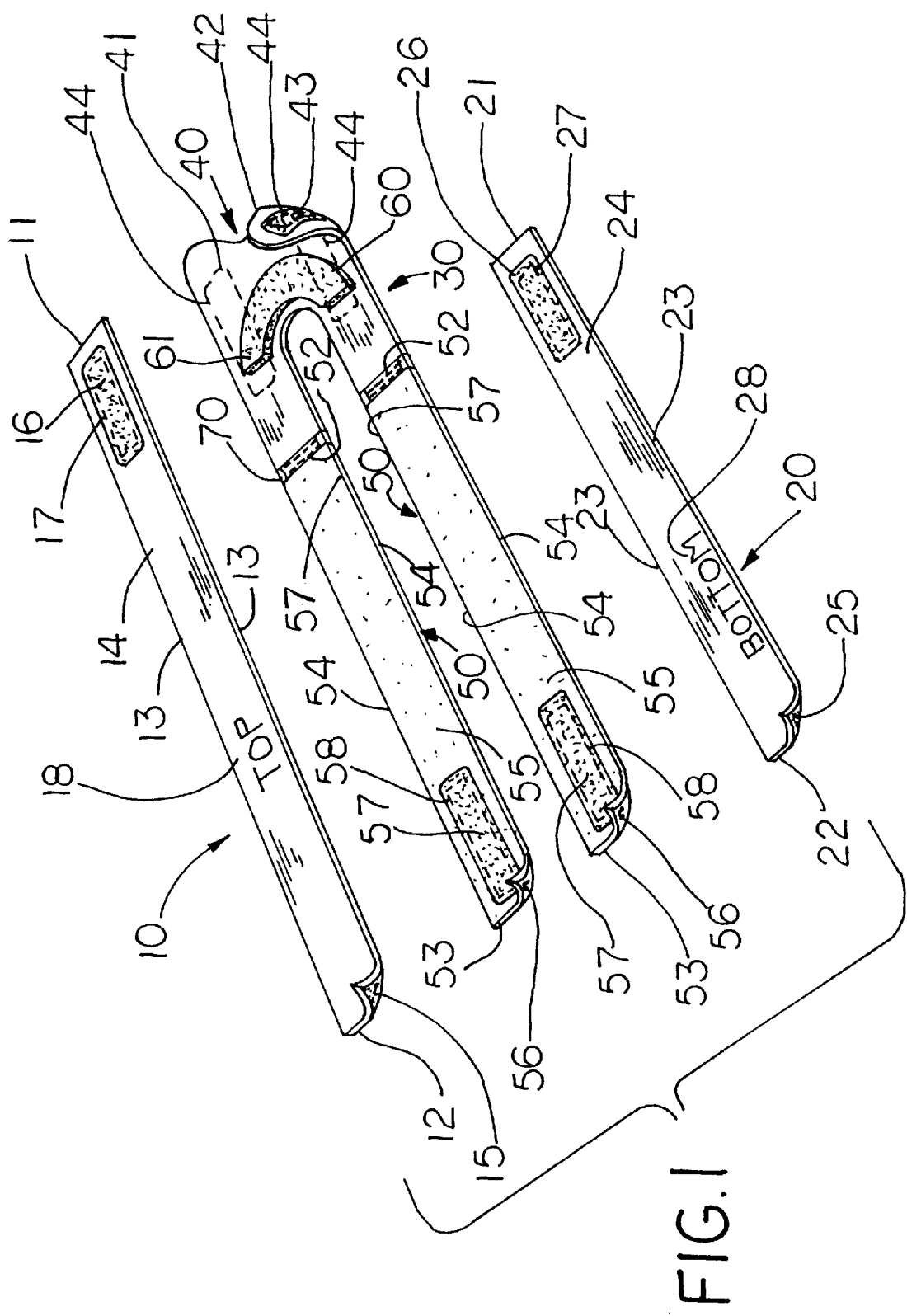
FIG. 1 is a perspective view of an orthopedic brace according to the present invention.

FIG. 1 is a perspective of view of the components of a brace according to the present invention. The brace generally comprises first strap 10, second strap 20, and support member 30. First strap 10 is a generally elongate member having first end 11, second end 12, opposed sides 13, first surface 14 and second surface 15. First strap 10 is preferably constructed of rubberized neoprene and covered on second surface 15 with the loop material portion of a hook and loop-type fastener. First strap 10 preferably has elastic properties. A hook portion 16 of hook and loop-type fastener is secured to first surface 14 of first strap 10 adjacent first end 11. In the embodiment shown, hook portion 16 is secured to first surface 14 by stitching 17. Stitching 17 extends completely through first strap 10. Alternatively, adhesive or any other means that will securely fasten hook portion 16 to first strap 10 may be used. A notation 18 is provided on first strap 10 to indicate its location relative to the body portion to be supported, as described below.

Second strap 20 is a generally elongate member having first end 21, second end 22, opposed sides 23, first surface 24 and second surface 25. Second strap 20 is shorter than first strap 10. Second strap 20 is preferably constructed of rubberized neoprene and covered on second surface 25 with the loop material portion of a hook and loop-type fastener. Second strap 20 preferably has elastic properties. A hook portion 26 of hook and loop-type fastener is secured to first surface 24 of first strap 20 adjacent first end 21. In the embodiment shown, hook portion 26 is secured to first surface 24 by stitching 27. Stitching 27 extends completely through second strap 20. Alternatively, adhesive or any other means that will securely fasten hook portion 26 to second strap 20 may be used. A notation 28 is provided on first strap 20 to indicate its location relative to the body portion to be supported, as described below.

Support member 30 includes a body portion 40 with two depending support straps 50 and a support pad 60. Body 40 includes a first surface 41 and a second surface 42. Body 40 is preferably manufactured from rubberized neoprene with the loop material portion of a hook and loop-type fastener disposed on second surface 42. Body 40 preferably has elastic properties. A pair of hook portions 43 of a hook and loop-type fastener are secured to bottom surface 42 by stitching 44. Stitching 44 extends completely through body 40. Alternatively, adhesive or other suitable means may be used to secure hook portions 43 to body 40.

Each support strap 50 includes a first end 51 secured to body 40. In the embodiment shown, support straps 50 are secure to body 40 by stitching 52. A piece of elastic 70 may be placed at the juncture of each end 51 with body 40 to bridge the juncture and stitching 52 may extend through elastic 70, as well as through first end 51 of each support strap 50 and body 40. Each support strap 50 further includes a free end 53, opposing sides 54, first surface 55 and second surface 56. Each support strap 50 is preferably manufactured from rubberized neoprene with a loop material portion of hook and loop-type fastener being secured to first surface 55. Support straps 50 preferably have elastic properties. Hook portions 57 of hook and loop-type fasteners are secured to each support strap 50 adjacent free ends 53. In the embodiment shown, hook portions 57 are secured to first surface 55 of support straps 50 by stitching 58. Stitching 58 extends completely through support straps 50. Alternatively, adhesive or any other means suitable to securely fix hook portions 57 to support straps 50 may be used.

Figure 2:
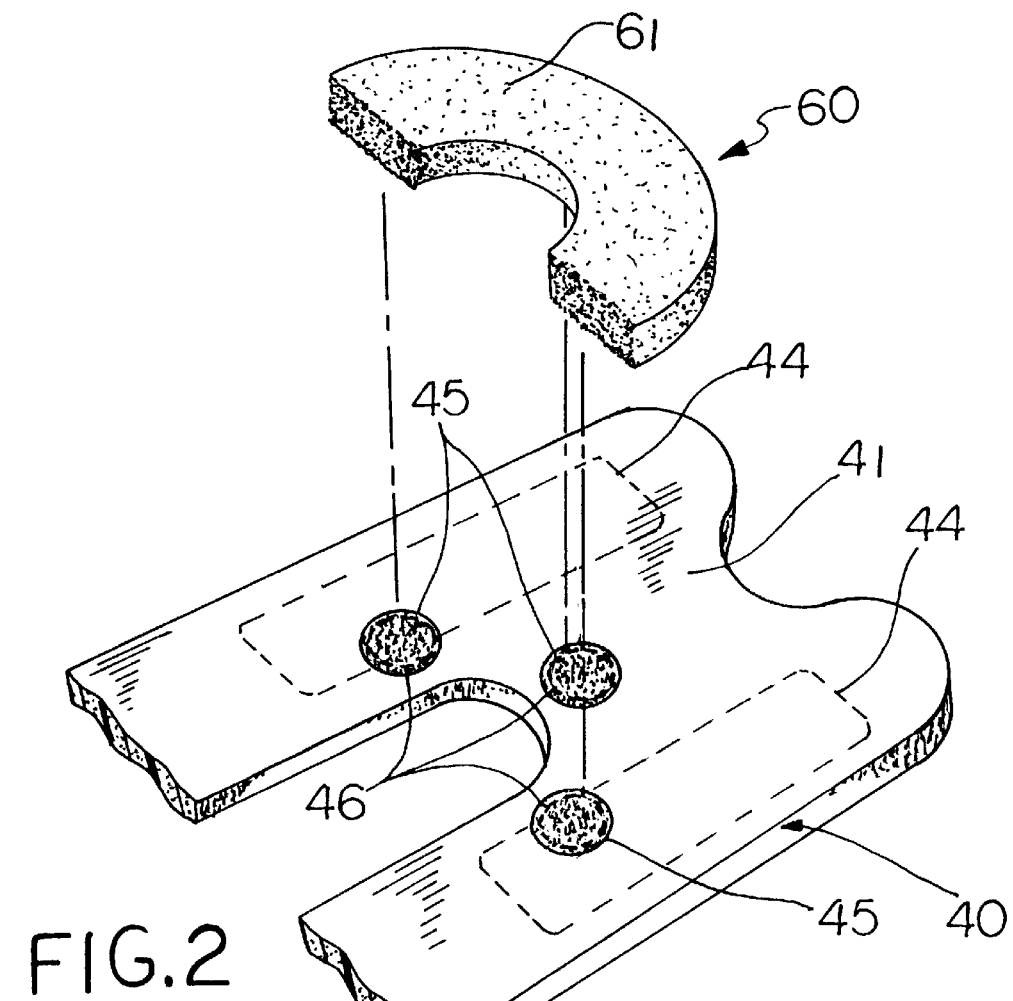
FIG. 2 is a detail of a portion of the orthopedic brace shown in FIG. 1.
Figure 3:
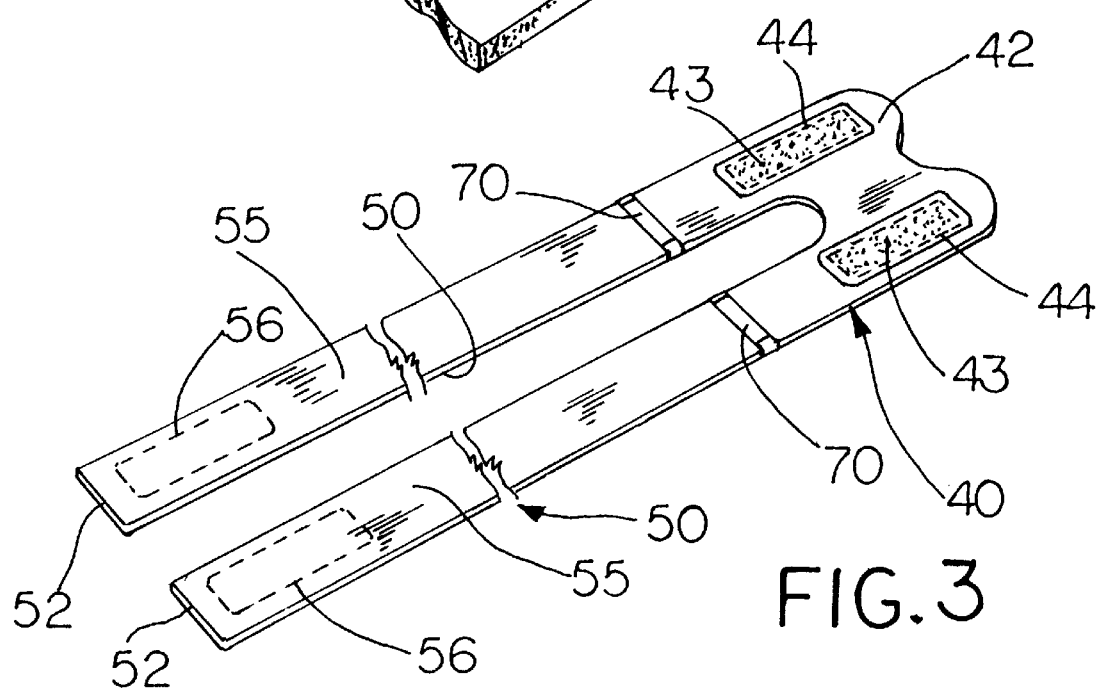
FIG. 3 is a bottom plan view of a component of the orthopedic brace shown in FIG. 1.

Support pad 60 is a generally horseshoe shaped member made of compressible material such as rubberized neoprene. Pad 60 is preferably covered with the loop material portion 61 of a hook and loop-type fastener. A plurality of hook portions 45 (FIG. 2) of hook and loop-type fastener may be provided on first surface 41 of body 40 for removably securing pad 60 thereto. Hook portions 45, in the embodiment shown, are secured to body 40 by stitching 46, which extends completely through body 40. Alternatively, adhesive or other means suitable for securing hook portions 45 may be used. Because pads 60 is removable, a plurality of pads 60 of varying sizes may be provided such that the same support member 30 may be utilized for body members of varying sizes. As an alternative to rubberized neoprene, pad 60 may be constructed of a gel-like substance having an outer membrane, commonly referred to as "memory gel". Hook material portions of a hook and loop-type fastener would be secured to the outer membrane so that such a pad 60 would also be removable from body 40.

Figure 4:
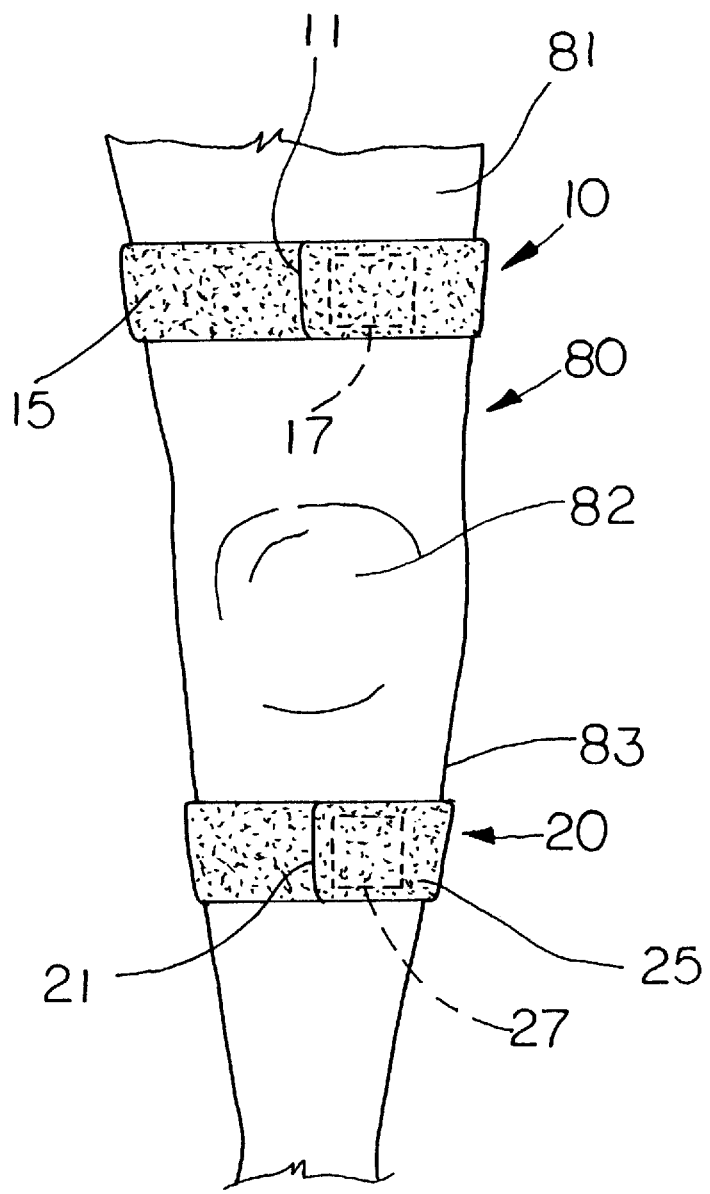
FIG. 4 is a perspective view showing the first step of applying the orthopedic brace shown in FIG. 1 to a human limb.

FIG. 4 shows the initial steps for securing the present invention to a limb. First strap 10 is positioned around thigh 81 of leg 80 above patella 82. To do so, first surface 14 of first strap 10 is placed on thigh 81 and wrapped around thigh 81 upon itself. First end 11 is then secured to second surface 15 by engaging hook portion 16 with the loop material on second surface 15.

In similar fashion, second strap 20 is secured about calf 83 below patella 82. Second strap 20 is positioned around calf 83 of leg 80 below patella 82. To do so, first surface 24 of second strap 20 is placed on calf 83 and wrapped around calf 83 upon itself. First end 21 is then secured to second surface 25 by engaging hook portion 26 with the loop material on second surface 25.

Figure 5:
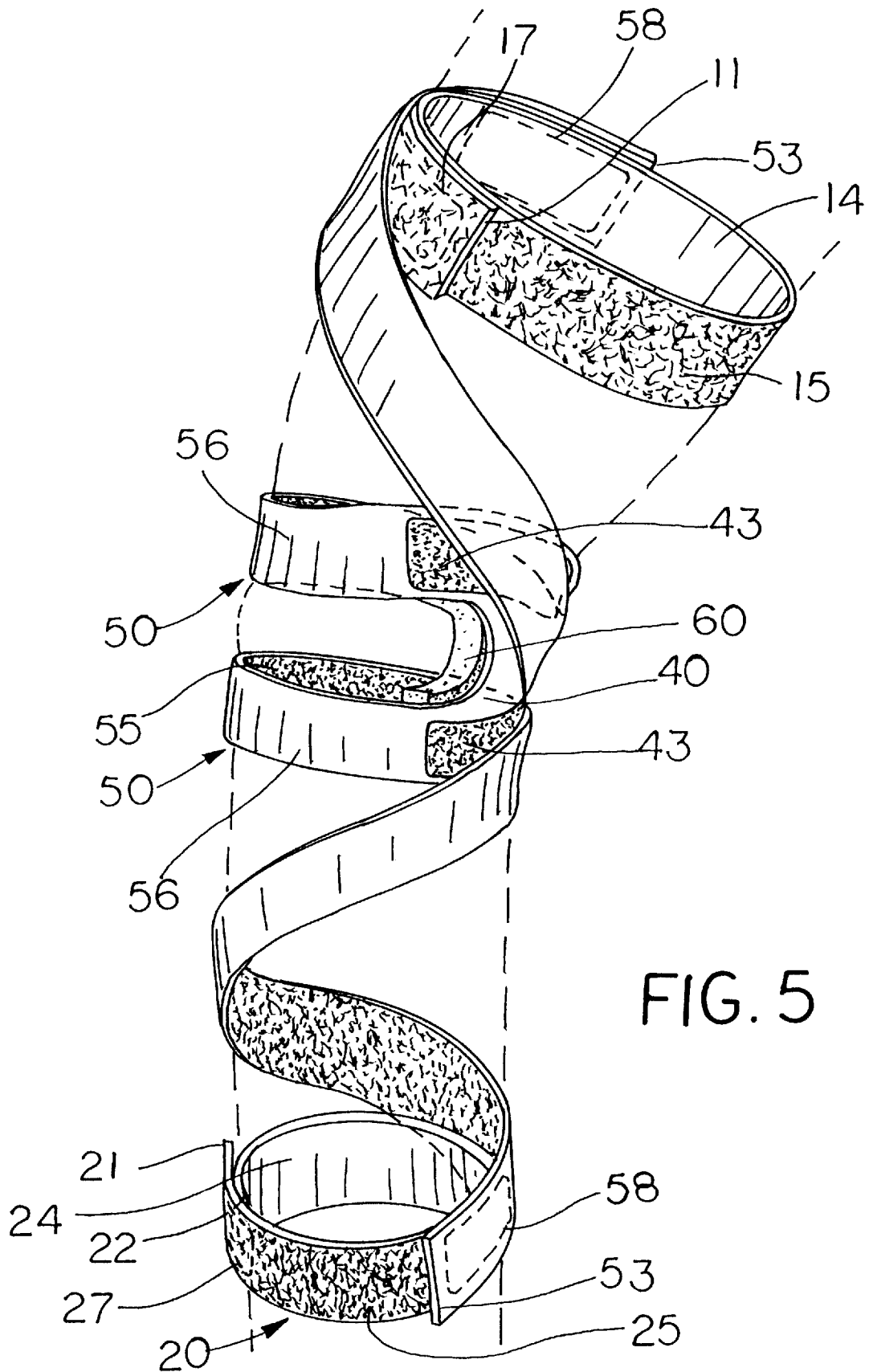
FIG. 5 shows the orthopedic brace shown in FIG. 1 applied to a human limb.

Once first strap 10 and second strap 20 have been secured about the limb, support member 30 is secured to the limb as shown in FIG. 5. Pad 60 is placed adjacent the medial side, for example, of patella 82 so as to apply force to patella 82 in the lateral direction. Support straps 50 are then wrapped about leg 80 so as to pull pad 60 into engagement with the medial side of patella 82. Once the desired force is applied to patella 82 the loop material on second surfaces 54 is engaged with a respective hook portion 43 on body 40. Support straps 50 are then further wrapped spirally around leg 80 such that one hook portion 57 engages loop material on second surface 15 of first strap 10 and the other hook portion 57 engages the loop material on second surface 25 of second strap 20. In this manner, support straps 50 do not exert a counter-acting force on support member 30 in a the medial. Rather, support straps 50 exert force on first strap 10 and second strap 20. Note that support member 30 may be applied to either the medial or lateral side of the patella to exert force as needed.

Although the present invention has been shown and described in detail, it is to be understood that the same is to be taken by way of example only and not by way of limitation. Numerous changes can be made to the embodiment described above without removing it from the scope of the present invention. For example, the shape of support member 30, as well as the relative sizes of the various components can be altered. Similarly, the location and shape of the hook and loop material segments may likewise be changed. Pad 60 can also be of a configuration other than that shown. First strap 10 and second strap 20 can be of any configuration sufficient to provide an anchor for support straps 50. Accordingly, the scope of the present invention is to be limited only by the following claims.

What is claimed is:

1. A knee brace, comprising:

a first strap encircling a portion of the leg above the knee;

a second strap encircling a portion of the leg below the knee;

a support member providing a support pad for engaging the patella;

a first support strap extending from said support member and encircling a portion of the leg above the knee;

a second support strap extending from said support member and encircling a portion of the leg below the knee;

said first support strap being attached to said first strap;

said second support strap being attached to said second strap; and a hook and loop-type fastener for attaching at least one of said support straps to at least one of said straps.

2. A knee brace according to claim 1, wherein said first and second straps are independent of said support member.

3. A knee brace according to claim 2, wherein said first support strap extends spirally up the leg to attach to said first strap and said second support strap extends spirally down the leg to attach to said second strap.

4. A knee brace according to claim 1, wherein said first, second and support straps are elastic.

5. A knee brace according to claim 1, wherein said support member is reversible to allow said support pad to engage the patella from either the lateral or medial side.

6. A knee brace according to claim 1, wherein said first support strap extends spirally up the leg to attach to said first strap and said second support strap extends spirally down the leg to attach to said second strap.

7. A knee brace according to claim 1, wherein said first support strap encircles a portion of the leg, attaches to said support member and extends spirally up the leg to attach to said first strap and said second support strap encircles a portion of the leg, attaches to said support member and extends spirally down the leg to attach to said second strap.

8. A knee brace, comprising:
   a first anchor for attachment to the leg above the knee;
   a second anchor for attachment to the leg below the knee;
   a support member providing a support pad for engaging the patella;
   a first support strap for attaching said support member to said first anchor;
   a second support strap for attaching said support member to said second anchor; and
   a hook and loop-type fastener for attaching at least one of said support straps to at least one of said anchors.

9. A knee brace according to claim 1, wherein said first and second anchors are independent of said support member.

10. A knee brace according to claim 9, wherein said first support strap extends spirally up the leg to attach to said first anchor and said second support strap extends spirally down the leg to attach to said second anchor.

11. A knee brace according to claim 1, wherein said first, second and support straps are elastic.

12. A knee brace according to claim 1, wherein said support member is reversible to allow said support pad to engage the patella from either the lateral or medial side.

13. A knee brace according to claim 1, wherein said first support strap extends spirally up the leg to attach to said first anchor and said second support strap extends spirally down the leg to attach to said second anchor.

14. A knee brace according to claim 1, wherein said first support strap encircles a portion of the leg, attaches to said support member and extends spirally up the leg to attach to said first anchor and said second support strap encircles a portion of the leg, attaches to said support member and extends spirally down the leg to attach to said second anchor.

15. A knee brace, comprising:
   a first strap encircling a portion of the leg above the knee;
   a second strap encircling a portion of the leg below the knee;
   a support member providing a support pad for engaging the patella;
   a first support strap extending from said support member and encircling a portion of the leg above the knee;
   a second support strap extending from said support member and encircling a portion of the leg below the knee;
   said first support strap extending spirally up the leg to attach to said first strap; and
   said second support strap extending spirally down the leg to attach to said second strap.

16. A knee brace according to claim 15, wherein said first and second straps are independent of said support member.

17. A knee brace according to claim 15, wherein said first, second and support straps are elastic.

18. A knee brace according to claim 15, wherein said support member is reversible to allow said support pad to engage the patella from either the lateral or medial side.

19. A knee brace according to claim 15, wherein said first and second support straps attach to said support member.

20. A knee brace, comprising:
   a first strap encircling a portion of the leg above the knee;
   a second strap encircling a portion of the leg below the knee;
   a reversible support member providing a support pad for selectively engaging the patella from either the lateral or medial side;
   a first support strap extending from said support member and encircling a portion of the leg above the knee;
   a second support strap extending from said support member and encircling a portion of the leg below the knee;
   said first support strap being attached to said first strap; and
   said second support strap being attached to said second strap.

21. A knee brace according to claim 20, wherein said first and second straps are independent of said support member.

22. A knee brace according to claim 20, wherein said first, second and support straps are elastic.

23. A knee brace according to claim 20, wherein said first support strap extends spirally up the leg to attach to said first strap and said second support strap extends spirally down the leg to attach to said second strap.

24. A knee brace according to claim 20, wherein said first support strap encircles a portion of the leg, attaches to said support member and extends spirally up the leg to attach to said first strap and said second support strap encircles a portion of the leg, attaches to said support member and extends spirally down the leg to attach to said second strap.

25. A knee brace, comprising:
   a first anchor for attachment to the leg above the knee;
   a second anchor for attachment to the leg below the knee;
   a reversible support member providing a support pad for selectively engaging the patella from either the lateral or medial side;
   a first support strap for attaching said support member to said first anchor; and
   a second support strap for attaching said support member to said second anchor.

26. A knee brace according to claim 25, wherein said first and second anchors are independent of said support member.

27. A knee brace according to claim 25, wherein said anchors and support straps are elastic.

28. A knee brace according to claim 25, wherein said first support strap extends spirally up the leg to attach to said first anchor and said second support strap extends spirally down the leg to attach to said second anchor.

29. A knee brace according to claim 25, wherein said first support strap encircles a portion of the leg, attaches to said support member and extends spirally up the leg to attach to said first anchor and said second support strap encircles a portion of the leg, attaches to said support member and extends spirally down the leg to attach to said second anchor.

30. A knee brace, comprising:
   a first anchor for attachment to the leg above the knee;
   a second anchor for attachment to the leg below the knee;

a support member providing a support pad for engaging the patella;

a first support strap for extending spirally up the leg to attach to said first anchor; and a second support strap for extending spirally down the leg to attach to said second anchor.

31. A knee brace according to claim 30, wherein said first and second anchors are independent of said support member.

32. A knee brace according to claim 30, wherein said anchors and support straps are elastic.

33. A knee brace according to claim 30, wherein said support member is reversible to allow said support pad to engage the patella from either the lateral or medial side.

34. A knee brace according to claim 30, wherein said first and second support straps attach to said support member.

* * * * *